United States Patent [19]

Kass

[11] Patent Number: 4,769,021

[45] Date of Patent: Sep. 6, 1988

[54] ABSORPTIVE PADS AND METHOD OF MAKING

[75] Inventor: Edward H. Kass, Lincoln, Mass.

[73] Assignee: President and Fellows of Harvard College, Cambridge, Mass.

[21] Appl. No.: 39,790

[22] Filed: Apr. 17, 1987

Related U.S. Application Data

[63] Continuation of Ser. No. 740,217, Jun. 3, 1985, abandoned, which is a continuation-in-part of Ser. No. 714,095, Mar. 20, 1985, abandoned.

[51] Int. Cl.[4] ............................................. A61F 13/16
[52] U.S. Cl. .................................. 604/367; 604/358; 128/156
[58] Field of Search ............................... 128/155–156; 604/904, 358, 360, 367, 348, 375, 359; 424/28

[56] References Cited

U.S. PATENT DOCUMENTS

| 2,134,930 | 11/1938 | Reynolds | 604/904 |
| 3,121,427 | 2/1964 | Mosier | 604/368 |
| 4,058,124 | 11/1977 | Yen et al. | 604/368 |
| 4,576,817 | 3/1986 | Montgomery et al. | 128/156 |
| 4,617,326 | 10/1986 | Bjornberg et al. | 604/367 |

Primary Examiner—C. Fred Rosenbaum
Assistant Examiner—Gene B. Kartchner

[57] ABSTRACT

Inclusion of salt of non-toxic divalent magnesium cation in absorptive pads, e.g., catamenial tampons, inhibits production of toxic shock syndrome toxin-1 during use.

20 Claims, No

ABSORPTIVE PADS AND METHOD OF MAKING

This is a continuation of application Ser. No. 740,217 filed June 3, 1985, entitled Absorptive Pads and Method of Making, now abandoned, which is a continuation-in-part of application Ser. No. 714,095, filed Mar. 20, 1985, now abandoned.

This invention relates to catamenial tampons, surgical and wound dressings and packings, and surgical sponges, hereinafter collectively referred to as absorptive pads, and pertains more specifically to such pads effective to substantially inhibit increased production of toxic shock syndrome toxin-1 and other toxic staphylococcal products during use, and to the method of making such pads.

Absorptive pads comprising a mass of solid water-insoluble water-absorbent material formed into the desired configuration for application to or insertion into a wound or a body cavity and adapted for absorption and retention of body fluids have been used for many years. Cotton fibers and semi-synthetic fibers such as cellulose derivatives including acetate rayon, viscose rayon, polyacrylate rayon, and polyurethane, polyester and other fibers have been widely used in the manufacture of such absorptive pads as well as various non-fibrous water-absorbent materials, particularly cellulose derivatives such as carboxymethyl cellulose, synthetic polymers such as those water-swellable cross-linked polymers capable of forming hydrogels, polyurethane sponges, and others. While such absorptive pads provide high capacity absorption and retention characteristics, and hence provide extended periods of protection during use of the absorptive pads, such extended use has increased the time period during which possible bacterial growth and production of toxin can occur in the vicinity of the absorptive pad, particularly in the case of catamenial tampons. Toxic shock syndrome is a severe disease which has been found to be associated with toxic shock syndrome toxin-1, a staphyloccus-produced toxin, and has been associated with use of certain brands of tampons, as well as the use of certain nasal and other surgical packings.

It has now been found that certain low concentrations of magnesium ion, below the concentration normally present in body fluids such as blood, are critical for optimal production of toxic shock syndrome toxic-1 and other staphylococcus products, some of which may be toxic, and it has also been found that various absorptive pad materials have the capability to absorb or bind magnesium ions.

The present invention provides an absorptive pad, and particularly a catamenial tampon, comprising water-sorptive material and an amount of non-toxic salt of a divalent magnesium cation effective to substantially inhibit production of toxic shock syndrome toxin-1 and other staphylococcal products during use of said absorptive pad. The invention also provides, in the method of making an absorptive pad which comprises forming a pad from a mass of water-sorptive water-insoluble solid material, the improvement which comprises including with said mass of material an amount of non-toxic salt of a divalent magnesium cation effective to substantially inhibit production of toxic shock syndrome toxin-1 or other staphylococcal products during use of said pad. The invention also provides the method of making an absorptive pad comprising water-sorptive solid material which comprises including said material a sufficient amount of a non-toxic divalent magnesium cation to satisfy the magnesium absorption or binding capacity of said material, and forming said material into said pad; and it provides an absorptive pad, particularly a catamenial tampon, having its magnesium-absorbing or binding capacity satisfied with a non-toxic divalent magnesium cation.

Any non-toxic salt can be used provided it is sufficiently water-soluble to provide the desired quantity of divalent magnesium cations to saturate the magnesium absorbing or binding capacity of the absorptive pad material; the absorbing or binding capacity varies widely depending upon the identity of the particular materials present in a pad as well as upon the manufacturing procedures followed in each case. In the case of polyacrylate rayon fibers, for example, 1000 micrograms of magnesium acetate or even less per gram of fiber suffices.

In general, an amount of salt effective to inhibit production of toxic shock syndrome toxin-1 or other toxic staphylococcal product during the use of an absorptive pad to a level no greater than that normally present in the absence of a pad will be sufficient to satisfy the magnesium absorbing or binding capacity of the pad. Suitable salts include those of magnesium. The anionic portion of the salt is not critical and may vary widely since very low solubility in water suffices for the purpose of the present invention. Suitable salts include the chlorides, sulfates, nitrates, acetates, palmitates, stearates, mandelates, hippurates, and the like, their magnesium salts being preferred. Magnesium stearate and magnesium acetate are particularly preferred.

The salt may be incorporated in the tampon by immersing the completed pad in an aqueous solution or dispersion of the salt, but it is usually more convenient and effective to treat one or more of the component materials with the desired salt at some point in the manufacturing procedure before or during incorporation of the material in the pad. For example, in the case of synthetic fiber materials, the fibers can be passed through an aqueous bath containing a suitable salt, or the fibers can be passed through a pair of squeeze rolls to which a supply of salt solution is supplied. Magnesium stearate is a preferred salt for application to synthetic fibers because it facilitates processing of the fibers. It is also possible to incorporate the desired salt in a portion only of the pad, for example in the outer wrapper, so that it is in position to be distributed or diffused under conditions of use to those other portions of the pad which require saturation of their magnesium absorbing or binding capacity. It is preferred, however, that the magnesium absorbing or binding capacity of all components of the pad be satisfied initially, before use of the pad.

An excess of salt above the amount required to saturate the magnesium absorbing or binding capacity of the absorbent material is not harmful, and there is no critical upper limit on the amount of salt employed in order to inhibit production of the toxin.

While it is not intended to limit this invention to any particular theory or mode of operation, it is believed that one or more of the water-sorptive solid materials normally present in pads such as tampons possesses sufficient absorptive or specific binding capacity for magnesium ions to reduce the concentration of such ions normally present in body fluids to a critical low level at which production of toxic shock syndrome toxin-1 and other toxic staphylococcal products is greatly enhanced, and that the present invention operates by eliminating this capacity.

What is claimed is:

1. An absorptive pad consisting essentially of water-sorptive material having magnesium chelating capability and an amount of non-toxic water-soluble salt of a divalent magnesium cation effective to substantially inhibit production of toxic shock syndrome toxin-1 during use of said pad.

2. A pad as claimed in claim 1 in which the amount of said divalent magnesium cation is at least sufficient to satisfy the magnesium-binding capacity of said pad.

3. A pad as claimed in claim 2 in which said salt is magnesium stearate.

4. A pad as claimed in claim 2 in which said salt is magnesium acetate.

5. A pad as claimed in claim 1 in which said pad is a catamenial tampon.

6. In the method of making an absorptive pad which comprises forming a pad from a mass of water-sorptive water-insoluble solid material having magnesium-chelating capability, the improvement which consists essentially of including with said mass of material an amount of non-toxic water-soluble salt of a divalent magnesium cation effective to substantially inhibit production of toxic shock syndrome toxin-1 during use of said pad.

7. The method as claimed in claim 6 in which the amount of said magnesium cation is at least sufficient to satisfy the magnesium-binding capacity of said pad.

8. The method as claimed in claim 6 in which said salt is magnesium stearate.

9. The method as claimed in claim 6 in which said salt is magnesium acetate.

10. The method as claimed in claim 6 in which said pad is a catamenial tampon.

11. The method as claimed in claim 10 in which said salt is magnesium acetate.

12. The method of making an absorptive pad comprising water-sorptive material having magnesium-chelating capability which consists essentially of including with said material an amount of a non-toxic water-soluble salt of magnesium divalent cation sufficient to satisfy the magnesium binding capacity of said material, and forming said material into a pad.

13. The method as claimed in claim 12 in which said pad is a catamenial tampon.

14. The method as claimed in claim 13 in which said salt is magnesium acetate.

15. An absorptive pad consisting essentially of water-sorptive material having magnesium-chelating capability and an amount of non-toxic water-soluble salt of a divalent magnesium cation at least sufficient to satisfy the magnesium binding capacity of said pad.

16. A pad as claimed in claim 15 in which said salt is magnesium stearate.

17. A pad as claimed in claim 15 in which said salt is magnesium acetate.

18. A pad as claimed in claim 15 in which said pad is a catamenial tampon.

19. A pad as claimed in claim 15 in which said pad is a catamenial tampon and said salt is magnesium stearate.

20. A pad as claimed in claim 15 in which said pad is a catamenial tampon and said salt is magnesium acetate.

* * * * *